United States Patent [19]

Panebianco et al.

[11] Patent Number: 5,125,916
[45] Date of Patent: Jun. 30, 1992

[54] STOMA CAP

[75] Inventors: Thomas Panebianco, Redington Shores, Fla.; Robert Seminara, Brooklyn, N.Y.; Stephen Crescimanno, Box 356, Chester, N.Y. 10918

[73] Assignees: RAS Partnership; Stephen Crescimanno

[21] Appl. No.: 680,315

[22] Filed: Apr. 4, 1991

[51] Int. Cl.⁵ .............................................. A61F 5/44
[52] U.S. Cl. .................................... 604/332; 604/328
[58] Field of Search ............... 604/332, 333, 328, 329, 604/334–345, 277, 278

[56] References Cited

U.S. PATENT DOCUMENTS 4,344,434 8/1982 Robertson ........................... 604/337

FOREIGN PATENT DOCUMENTS 1475608  4/1989  U.S.S.R. ............................. 604/337
9007311  7/1990  World Int. Prop. O. .......... 604/337

Primary Examiner—Randall L. Green
Assistant Examiner—R. Clarke
Attorney, Agent, or Firm—Fitzpatrick, Cella, Harper & Scinto

[57] ABSTRACT

An ostomy appliance is disclosed for selectively sealing a stoma. The appliance includes a central elongated relatively rigid tube having inner and outer end portions. A cap is support to the outer end portion of the tube and is adapted to engage the users skin when the tube is inserted in a stoma. A flexible extendable and collapsible bellows is mounted on the inner end of the tube for sealing the inside of the stoma when the appliance is inserted therein. A flexible rod insertable through the cap and tube for engagement with the bellows extends the bellows to collapse it for insertion in the stoma.

14 Claims, 4 Drawing Sheets

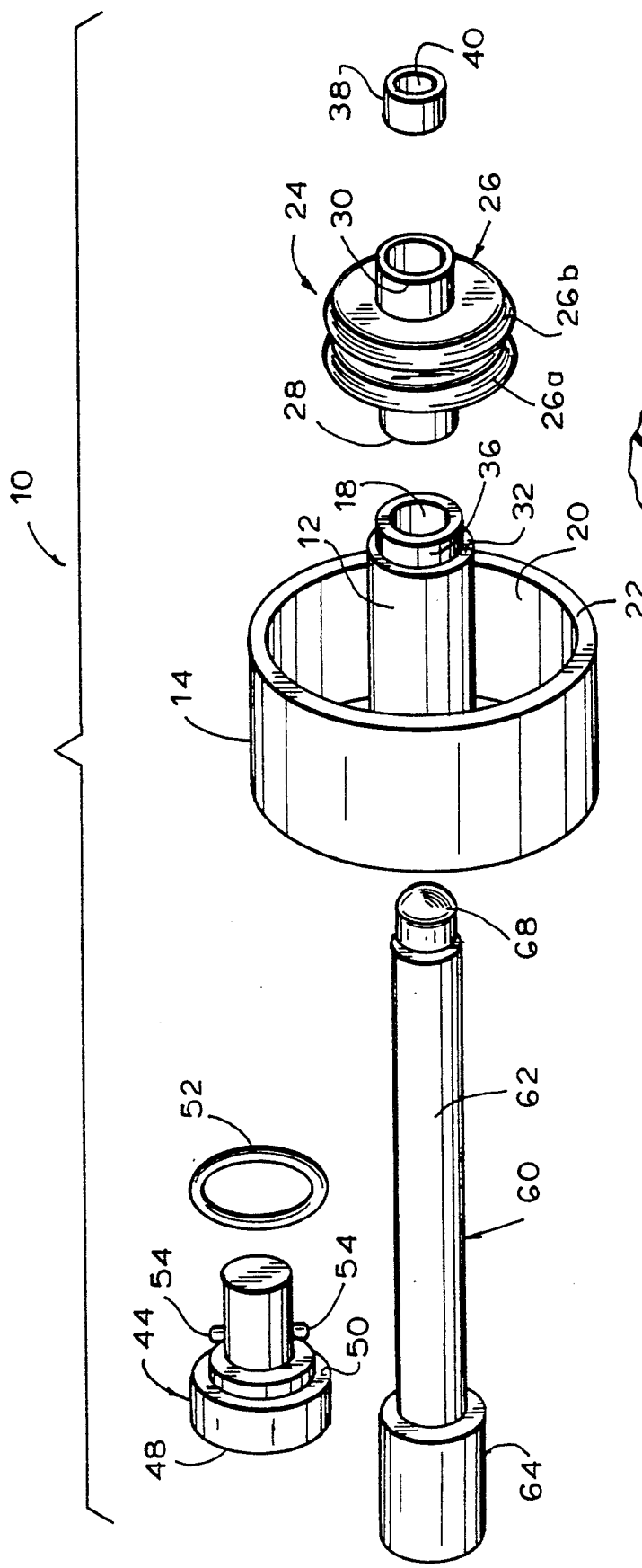
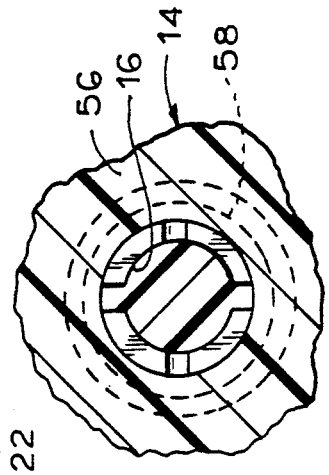

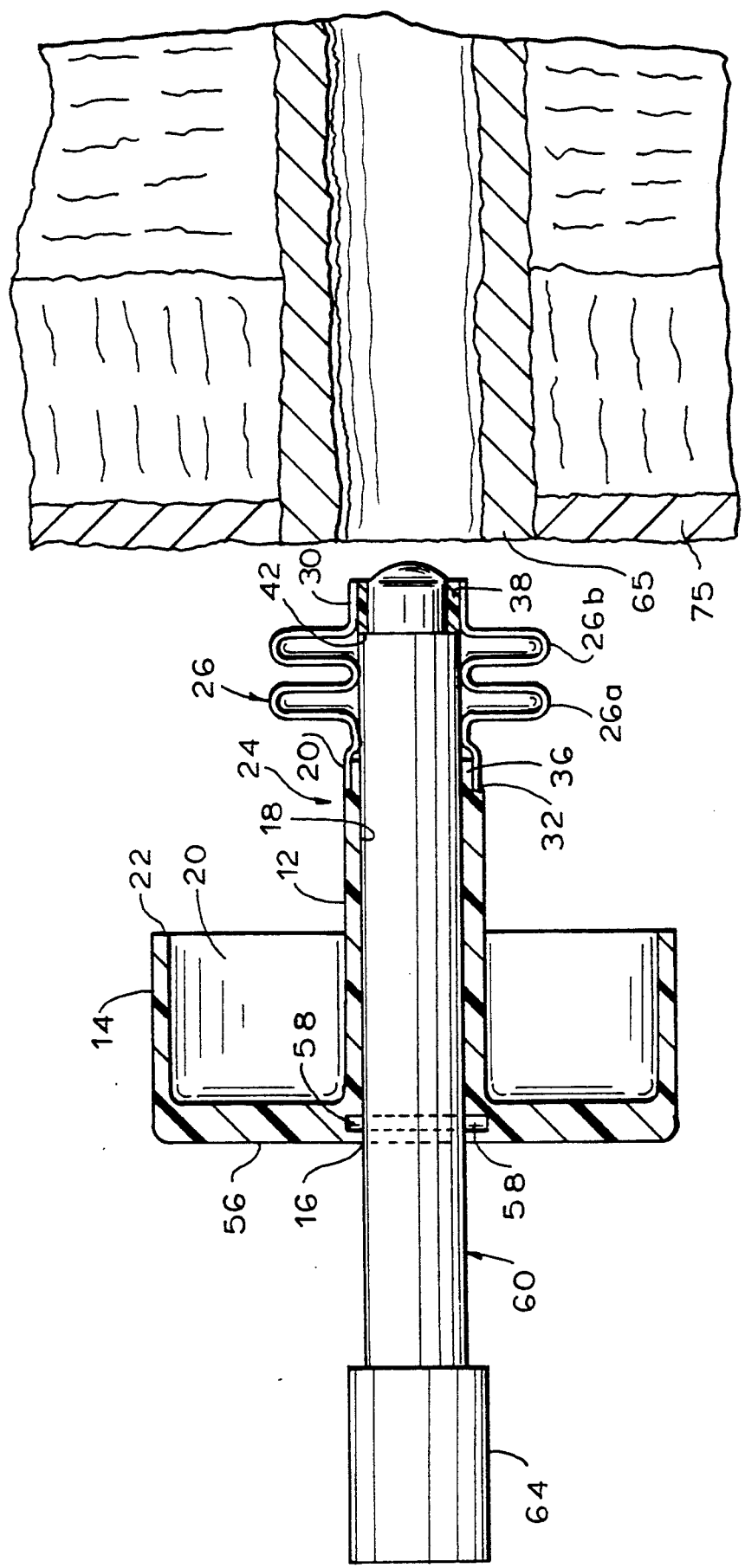

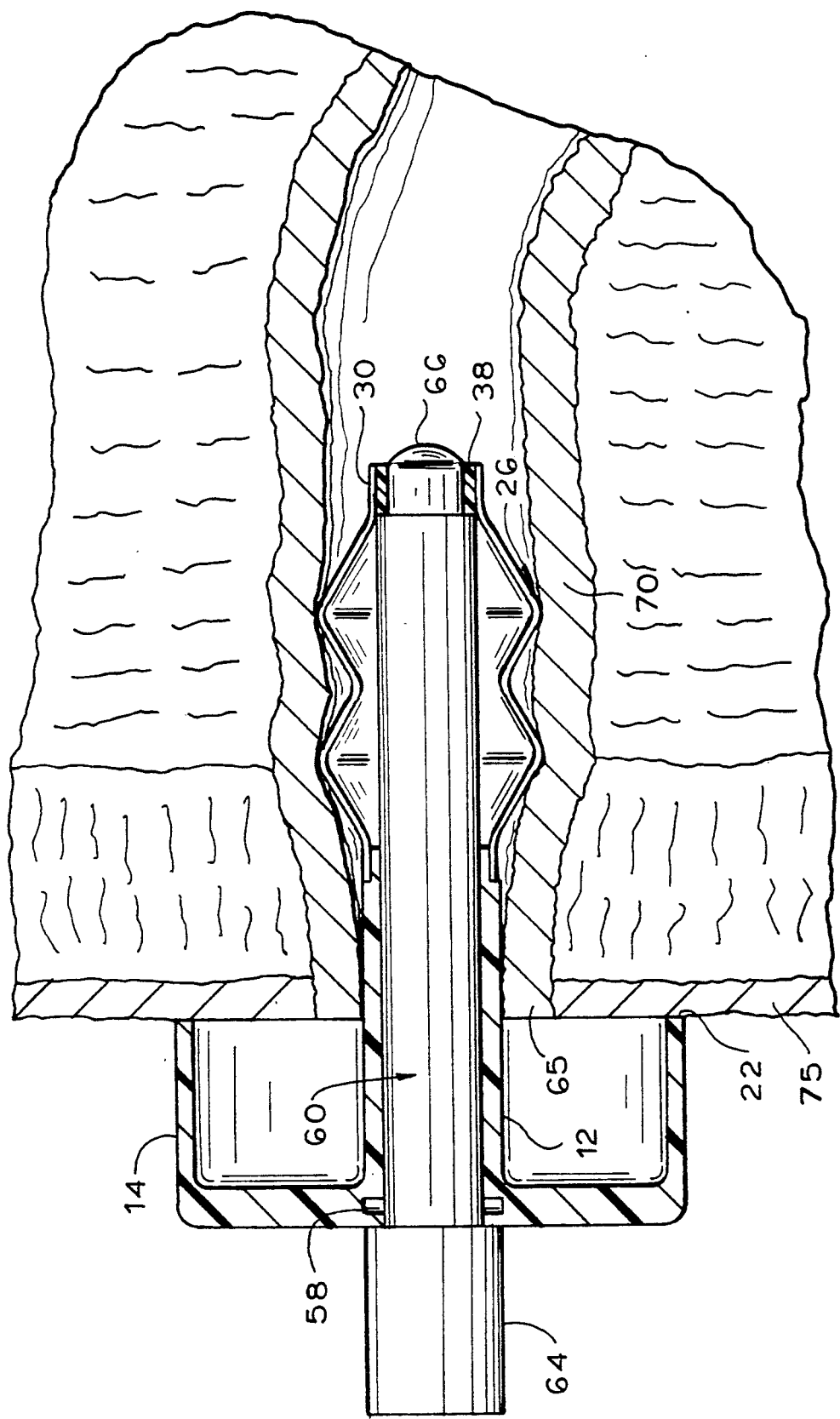

STOMA CAP

BACKGROUND OF THE INVENTION

The present invention relates to an ostomy appliance and more particularly an appliance adapted for ileostomy and colostomy use.

The use of appliances for occluding colostomies and ileostomies have been proposed in the past. Such devices are generally intended to permit the patient to be comfortable without continual use of a belt or bag or any other attachment on the surface of the body and to quickly rehabilitate a patient psychologically to normal life after his or her operation.

A colostomy is an operation on the lower bowels (rectum and anus) in which part of the bowel is removed surgically due to cancer or other malignant infections. The bowel is brought out by the surgeon through an opening in the side of the abdominal wall and surgically attached to the skin for the purpose of serving as a means for eliminating body waste. An ileostomy is a similar procedure on the small intestine.

The artificial body aperture or opening formed in an ileostomy or colostomy is referred to as a "stoma".

The patient who undergoes an ostomy operation has no control over passage of body waste materials, liquids, or gases through the intestine to the stoma. In the past pads and various receptacles such as bags and bag attachments have been taped over the opening or attached to the stoma by a belt around the body in order to cover the stoma and collect, but not control, the escape of body waste, liquids and gases. Such methods are inefficient, ineffective, and often embarrassing.

In the past, a variety of appliances have been proposed for occluding colostomies or ileostomies at the stoma. Such devices have taken a wide range of forms, but have been primarily of the inflatable cuff type. Such closures are shown for example in U.S. Pat. Nos. 4,721,508 and 4,344,434. These devices use inflatable cuffs and permit a degree of control over the escape of wastes through the appliance from the stoma into a bag or other collecting device. Other forms of inflatable devices, such as shown in U.S. Pat. No. 4,241,735, simply form a plug in the stoma.

It is believed that because of a variety of problems with such devices, they have rarely and infrequently been used. Inflatable devices are of particular concern because their inflatable cuffs can burst or be blown out when placed within the stoma and inflated. They also rely on artificial pressure to seal the inside of the stoma and are subjected to pressure losses and therefore leakage.

It is an object of the present invention to provide an ostomy appliance which is simple for a patient to self-install in a stoma.

Another object of the present invention is to provide an ostomy appliance which is reliable in use and which automatically seals the inside of the stoma once installed.

Another object of the present invention is to provide an ostomy occlusion appliance which is relatively simple and inexpensive to manufacture.

SUMMARY OF THE INVENTION

In accordance with an aspect of the present invention the ostomy appliance includes a generally cup shaped cap having a central opening formed therein and an integral elongated hollow tube. The tube has an internal bore which communicates with the opening in the cap and is dimensioned to be inserted in a stoma. A flexible hollow bellows is secured at one end to the inner end of the tube. The bellows has plastic memory and normally remains in its collapsed, maximum diameter position. The bellows is hollow and its inner end is opened to the interior of the body when installed so that body wastes, fluids and gasses can pass through the bellows, tube, and cap.

An insertion rod is provided to install the appliance in the stoma. The rod is dimensioned to fit through the cap opening end tube and engage the bellows in order to extend the bellows to reduce its size and permit insertion in the stoma. Upon withdrawal of the insertion rod the bellows automatically returns to its collapsed position as a result of its plastic memory, thereby engaging the interior surface of the stoma. The peristaltic pressure of fluids and gasses in the intestine hold the folds of the bellow closed against the stoma to form a tight seal therewith.

A separate closure element is provided to close the opening in the cap, so that the stoma is occluded. Thus the patient can control the expulsion of body waste, fluids and gasses from the stoma with the closure element.

BRIEF DESCRIPTION OF THE DRAWINGS

The above, and other objects, features and advantages of this invention will be apparent in the following detailed description of an illustrative embodiment thereof which is to be read in connection with the accompanying drawings wherein:

FIG. 1 is an exploded perspective view of the ostomy appliance of the present invention.

FIG. 2 is a side sectional view of the appliance of the present invention before insertion in the stoma;

FIG. 3 is a side view, similar to FIG. 2., but showing the ostomy appliance of the invention as it is installed in the stoma;

FIG. 5 is an end view of the appliance showing the bayonet look connection between the closure element and the cap.

DESCRIPTION OF THE PREFERRED EMBODIMENT

Figure 4:
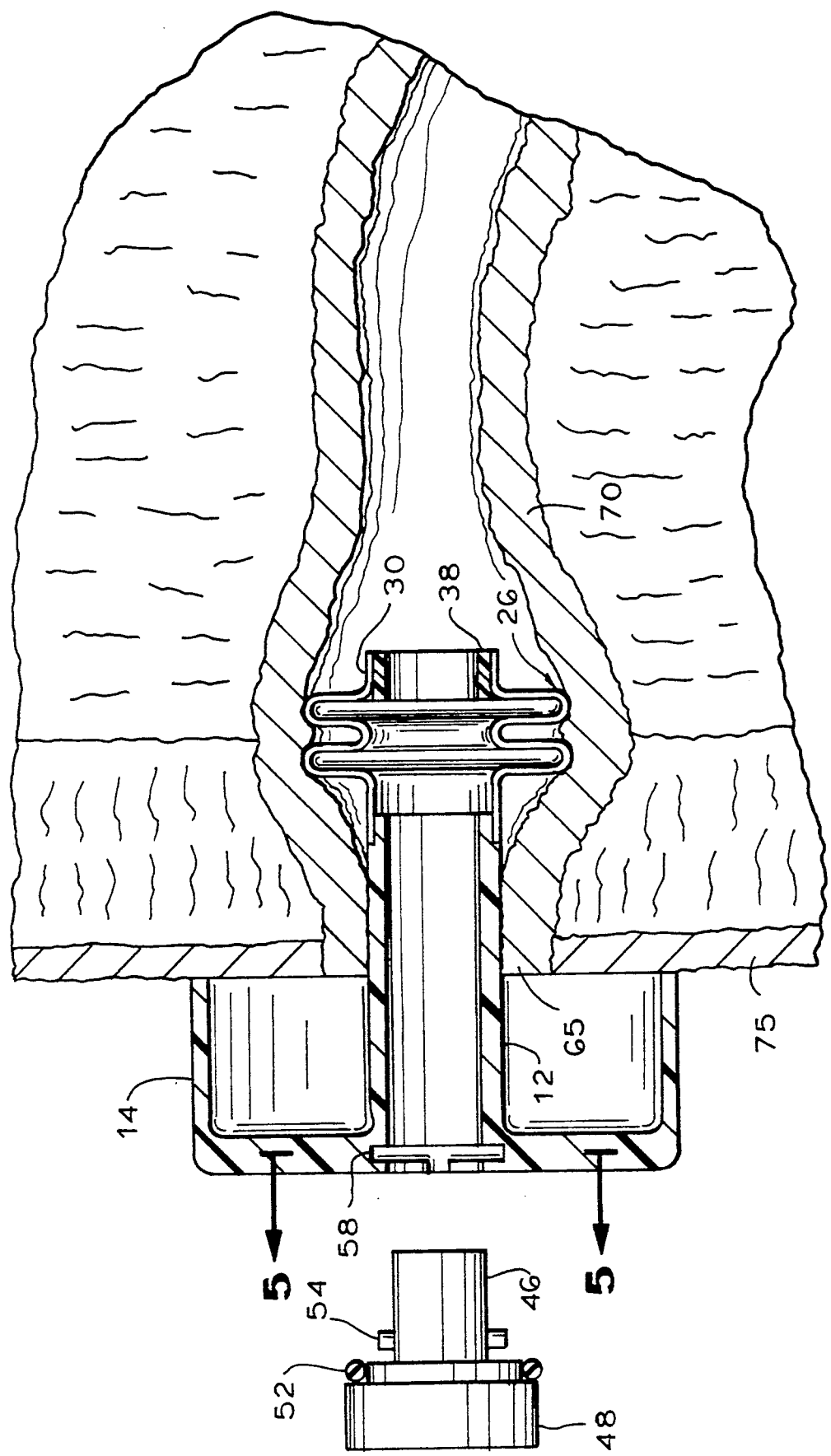
FIG. 4 is a side view, similar to FIG. 3, showing the configuration of the appliance in its final installed position with the insertion rod removed.

Referring now to the drawings in detail, and initially to FIG. 1 thereof, the ostomy appliance 10 of the invention is illustrated. As seen therein the ostomy appliance includes a central tube 12 integrally formed with a generally cup shaped cap 4. The cap 14 has a central opening 16 (FIG. 2) therein which aligns and communicates with the central bore 18 of tube 12. The cup shaped cap 14 has an open end 20 defining a peripheral edge 22 which is dimensioned to engage the skin surface of the body of the patient when the device is installed in the stoma.

The inner end 24 of tube 12 has a collapsible bellows 26 mounted thereon. Bellows 26 is formed of a resilient flexible material such as polyurethane, rubber or thermoplastic, as desired. It is formed to have a plastic memory so that it will always return to its collapsed position as illustrated in FIG. 1. In the illustrative embodiment the bellows has two folds or bellow sections 26a and 26b which are generally circular and cross section. The bellows is hollow and has a pair of tubular extensions 28 and 3 at its opposite ends.

The inner end 24 of tube 12 has a shoulder 32 formed thereon defined by an undercut annular ring section 36. The inner end 28 of the bellows is adapted to fit over this ring section 36 and abut shoulder 32. Preferably the bellows is secured to the undercut portion of tube 12 by a suitable adhesive material or by sonic welding. The latter is preferred since it more surely eliminates the possibility of the bellows becoming disengaged from the tube upon withdrawal of the device from the stoma.

The outer end 30 of bellows 26 preferably includes an internal relatively rigid sleeve 38 having a central bore 40 therein which communicates with the interior of the bellows. The sleeve 40 defines an internal shoulder or edge 42 which cooperates with the insertion tool described hereinafter in order to install the appliance in the stoma. Preferably sleeve 38 is also sonically welded to the bellows.

The central opening 16 in cap 14 is adapted to be closed by a plug or closure member 44. This closure includes a stem 46, an enlarged head portion 48, and a shoulder portion 50 which defines a seat for an 0 ring 52 formed of rubber or elastomer. Stem 46 of closure 44 includes a pair of bayonet locking fingers 54 extending perpendicularly therefrom.

The base 56 of cap 14, in which the opening 16 is formed, includes opposed bayonet locking grooves 58 formed therein in a conventional manner. These grooves are adapted to receive and engage the pins 54 to hold the cap in place when stem 46 is inserted in opening 16.

In order to install the appliance in the stoma, an installation rod 60 is provided. This rod is formed of a semi-rigid flexible plastic material and has a mainstem portion 62 and a finger grip portion 64. The mainstem portion 62 of the installation rod is dimensioned to fit through the opening 16 in the cap and the central bore 18 of the tube 12. Preferably the diameter of grip portion 64 is greater than the diameter of opening 16. The inner end 66 of rod 60 has a reduced diameter portion to define a shoulder 68 thereon. This shoulder is adapted to engage shoulder 42 of the sleeve 38 in bellows 16.

In order to install the appliance of the present invention the cap 44 is removed, and installation rod 60 is inserted through the opening 16 in the cap to engage the shoulder 68 with shoulder 42 of sleeve 38. Rod 60 is longer than tube 12. This permits the user to push against the rod to extend the bellows, to the extended position illustrated in FIG. 3. As a result of this extension of the bellows the outermost dimension of the bellows is reduced and the device can easily be installed through the stoma 65 formed by the intestine 70. The appliance is pushed into the stoma 65 until the edge 22 of the cap 14 engages the surface of the patient's skin 75. This defines the limiting position for the user.

Tube 12 is dimensioned such that its length is sufficient to pass through the layer of the body formed by the skin 75 and internal muscle tissue 72, as illustrated in FIG. 3. This positions the bellows in the stoma within the adjacent body cavity.

Once the cap is engaged in the skin the installation rod 60 is simply withdrawn. Disengagement of the rod from the shoulder 42 in the bellows permits the bellows to collapse towards its original position as a result of its plastic memory. This increases the diameter of the bellows and urges the edges of the bellows against the internal surface of the intestine 70 at the stoma. In addition to the natural resiliency of the bellows, the peristaltic pressure of liquids and gasses within the intestine will urge the bellows against the surface of the intestine to form a tight seal therewith.

Because the bellows has an open outer end body fluids, waste, and gasses can pass through the bellows, to the stem 12 and out of the cap opening 16. Typically the patient will install the closure element 44 in the opening 16 of the cap in order to occlude the stoma. This will prevent undesired and uncontrolled discharge of waste, body fluids and gas. Should the patient feel the need to relieve gas pressure from the intestine, it is a simple matter for him or her to twist the closure element from its bayonet locked position to its installation position without removing the closure. This will break the seal and permit gas to be expelled from the ostomy, but not waste. When it is desired or necessary to relieve body fluids and waste, the patient removes plug 44 and attaches a conventional bag to the skin by an adhesive or the like until the waste is passed. The bag is then removed and the closure reinstalled. Alternatively, the bag can be connected directly to the cap 14 by an adhesive tape or elastic band.

Ostomy appliances of the type described therein have been tested in human patients and found to be entirely successful, particularly for early colostomy patients. It is contemplated that the ostomy appliance of the invention would be supplied in different sizes for different patients and for use in ileostomies and colostomies. It is anticipated that size variances of 0.5 cm in diameter should be sufficient.

By constructing the ostomy appliance of the invention with the cap 14, as described above, an additional safeguard against leakage is prevented. The edge 22 of the cap forms a seal against the skin such that if any leakage of fluid or waste does pass the bellows, it will pass through the stoma into the cap. The combination of the pressure of the bellows against the interior of the skin with the cap on the exterior of the skin holds the appliance safely in place and forms a sufficiently tight seal for the cap against the skin to prevent leakage.

It is preferred that the appliance be removed each evening by the patient and cleaned. This is accomplished by reversing the installation steps, i.e. removing cap 44, inserting rod 60 to extend the bellows and withdrawing the appliance with the rod fully inserted.

Although the bellows is formed of a material that has plastic memory, it is preferred that the diameter of the tip portion 66 of the insertion tool form a fairly tight fit with the internal surface of the sleeve 38, so that when the rod is withdrawn frictional forces between these two surfaces aid in pulling the bellows back towards the surface of the stoma.

In addition, although the bellows, as illustrated in the illustrative embodiment, is shown as a separate element, sonically welded to tube 22 and to sleeve 38, it is contemplated that with appropriate materials the bellows could be integrally molded with the tube 12 in the same plastic material.

Although an illustrative embodiment of the present invention has been described herein with reference to the accompanying drawings, it is to be understood that this invention is not limited to such embodiment and that various changes and modifications can be effective therein without departing from the scope or spirit of this invention.

What is claimed is;

1. An ostomy appliance comprising a central elongated relative rigid tube having inner and outer end portions, a cap secured to the outer end portion of the tube and adopted to engage the users skin when said tube is inserted in a stoma and a flexible extendable and collapsible bellows mounted on the inner end portion of said tube for sealing the inside of the stoma when said appliance is inserted therein; said bellows having plastic memory and being selectively extendible from a collapsed bellows configuration to an extended configuration wherein its outermost dimension is less than that of the bellows configuration and permits insertion of the bellows in a stoma, whereupon the bellows returns to its collapsed position after insertion in the stoma, due to its plastic memory and seals the inside of the stoma.

2. An ostomy appliance comprising a central elongated relative rigid tube having inner and outer end portions, a cap secured to the outer end portion of the tube and adopted to engage the users skin when said tube is inserted in a stoma and a flexible extendable and collapsible bellows mounted on the inner end portion of said tube for sealing the inside of the stoma when said appliance is inserted therein, and removable means for extending said bellows to permit insertion of the bellows and tube in the stoma, said bellows returning to its collapsed position upon removal of said means thereby to seal the inside of the stoma.

3. An ostomy appliance as defined in claim 2 wherein said cap has a central opening formed therein communicating with the interior of said tube and wherein the bellows has a central opening communicating with the interior of said tube thereby to permit drainage of the ostomy.

4. An ostomy appliance as defined in claim 3 including removable closure means for closing the central opening in the cap.

5. An ostomy appliance as defined in claim 4 wherein said cap and closure means include cooperating bayonet lock means.

6. An ostomy appliance as defined in claim 4 wherein said cap is generally cup shaped having its open end directed toward the inner end of said tube and defining an edge adopted to engage the users skin when the appliance is installed in the stoma.

7. An ostomy appliance as defined in claim 3 wherein said means for extending the bellows comprises an elongated rod adopted to be received through the central opening of the cap and the exterior of the tube, said rod being longer than the tube and having an inner end, said inner end of the rod and said bellows having cooperating engagement means arranged such that upon insertion of the rod in the appliance and engagement with the bellows the bellows is extended to reduce its diameter and permit insertion in the stoma.

8. An ostomy appliance comprising a generally cup shaped cap having a central opening formed therein and an integral elongated hollow tube having an internal bore communicating with said opening, said tube having an inner end and being dimensioned to be inserted in a stoma, a flexible bellows having plastic memory and opposed first and second ends, said bellows being secured at its first end to the inner end of the tube with its interior communicating with the interior of the tube and having an opening in its second end, said bellows being selectively extendable to reduce its outermost dimension to permit insertion of the bellows and tube in a stoma whereupon the bellows returns to its collapsed position due to its plastic memory and seals the inside of the stoma, and removable closure means for said cap opening.

9. An ostomy appliance as defined in claim 8 including removable means for extending said bellows to permit insertion of the bellows and tube in the stoma, said bellows returning to its collapsed position upon removal of said means to seal the inside of the stoma.

10. An ostomy appliance as defined in claim 9 wherein wherein said cap and closure means include cooperating bayonet lock means.

11. An ostomy appliance as defined in claim 10 wherein said cap is generally cup shaped having its open end directed toward the inner end of said tube and defining an edge adopted to engage the users skin when the appliance is installed in the stoma.

12. An ostomy appliance as defined in claim 11 including means for selectively extending said bellows.

13. An ostomy appliance as defined in claim 12 wherein said means for extending the bellows comprises an elongated rod adopted to be received through the central opening of the cap and the exterior of the tube, said rod being longer than the tube and having an inner end, said inner end of the rod and said bellows having cooperating engagement means arranged such that upon insertion of the rod in the appliance and engagement with the bellows the bellows is extended to reduce its diameter and permit insertion in the stoma.

14. An ostomy appliance as defined in claim 13 wherein said cooperating means comprised a shoulder formed or said inner end of the rod and a cooperating shoulder on the interior of as said second end of the bellows.

* * * * *